US00PP28329P3

(12) United States Plant Patent
Pilling et al.

(10) Patent No.: US PP28,329 P3
(45) Date of Patent: Aug. 22, 2017

(54) ***PHILODENDRON* HYBRID PLANT NAMED 'PHIL01'**

(50) Latin Name: ***Philodendron* sp.**
Varietal Denomination: Phil01

(71) Applicants: Rob Pilling, Doonan (AU); Alison Pilling, Doonan (AU)

(72) Inventors: Rob Pilling, Doonan (AU); Alison Pilling, Doonan (AU)

( * ) Notice: Subject to any disclaimer, the term of this patent is extended or adjusted under 35 U.S.C. 154(b) by 42 days.

(21) Appl. No.: 14/757,057

(22) Filed: Nov. 13, 2015

(65) Prior Publication Data

US 2016/0143205 P1 May 19, 2016

Related U.S. Application Data

(60) Provisional application No. 62/079,808, filed on Nov. 14, 2014.

(51) Int. Cl.
*A01H 5/12* (2006.01)

(52) U.S. Cl.
USPC ..... Plt./381

(58) Field of Classification Search
USPC ..... Plt./381
See application file for complete search history.

*Primary Examiner* — Keith Robinson
(74) *Attorney, Agent, or Firm* — Samuel R. McCoy, Jr.

(57) ABSTRACT

'PHIL01' is a distinctive *Philodendron* cultivar which is characterized by the combination of a short plant height, a high degree of basal branching and small lanceolate foliage.

1 Drawing Sheet

Latin name of the genus and species: The Latin name of the genus and species of the novel variety disclosed herein is *Philodendron* sp.

Variety denomination: The inventive variety of *Philodendron* disclosed herein has been given the variety denomination 'PHIL01'.

BACKGROUND OF THE INVENTION

Parentage: The *Philodendron* cultivar 'PHIL01' is a chance seedling-discovered at a commercial nursery operation in Doonan, Queensland, Australia amongst a commercial crop of *Philodendron* sp. (parentage unknown) in January 2009. The seedling was observed to have a lanceolate leaf, a short plant height and dense growth habit whereas all other plants of the same crop had a lobed leaf and tall plant height which is characteristic of the parent. The plant was isolated for further evaluation and, in January of 2010, the cultivar was given the denomination of 'PHIL01'.

Asexual Reproduction: 'Phil01' was first asexually propagated in January of 2010 from leaf cuttings at a commercial nursery operation in Doonan, Queensland, Australia. After five generations of asexual reproduction and three years of growing trials 'Phil01' has remained stable and uniform with no off types observed.

SUMMARY OF THE INVENTION

'PHIL01' is a distinctive *Philodendron* cultivar which is characterized by the combination of a short plant height, a high degree of basal branching and small lanceolate foliage.

BRIEF DESCRIPTION OF THE FIGURES

The figure illustrates, as nearly true as it is reasonably possible to make the same in color illustrations of this type, an exemplary 18 month old 'PHIL01' plant, grown at a commercial nursery in Clarendon, New South Wales, Australia. The 'PHIL01' plant is shown with the parent plant, at the rear.

BOTANICAL DESCRIPTION OF THE PLANT

The following is a detailed botanical description of a new and distinct variety of a *Philodendron* ornamental plant known as 'PHIL01'. Unless indicated otherwise, the descriptions disclosed herein are based upon observations made from an 18 month old 'PHIL01' plant, established in a full-sun landscape in Clarendon, New South Wales, Australia. The observed plant was maintained with granular slow release fertilizer and regularly watered with overhead irrigation. No pest and disease measures were taken.

Those skilled in the art will appreciate that certain characteristics will vary with older or, conversely, younger plants. 'PHIL01' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 2001 edition. Note that generic color descriptions such as 'white' do not exist in the R.H.S. charts and the corresponding R.H.S. colors are quoted.

Plant description:

*Plant habit.*—Self-supporting, compact herbaceous perennial with a generally round shape, rapid rate of growth, and a high degree of basal branching.

*Height.*—Generally 200 mm, with tallest leaf measuring 300 mm.

*Width.*—450 mm.

*Bloom period.*—Not observed.

*Hardiness.*—USDA Zone 10 to 11.

*Propagation*.—Asexual propagation is accomplished by way of stem and leaf cuttings which root well without rooting compound or hormone.

*Time to develop roots*.—Approximately 21 days at 25 degrees Celsius.

*Crop time*.—Approximately 16 weeks are needed to produce a well rooted 15 cm nursery pot, starting from a rooted cutting. Crop time varies with location and production practices.

*Pest and disease susceptibility or resistance*.—Resistance to pathogens common to *Philodendron* has not been observed.

Roots: Strong root system. Main roots thick and fleshy; abundant thin lateral roots; mature roots are greyed-orange, nearest to a combination of 164B and 164C, and juvenile roots are yellow-white, 158A. Thick short aerial roots are occasionally observed; aerial roots are greyed-green, RHS 197B, and smooth.

Stem:

*General habit*.—Multiple main stems, basally branched; greater than 100 shoots per pot.

*Stem strength*.—Low to medium rigidity.

*Attitude*.—Erect to semi-erect.

*Stem cross-section*.—Round.

*Stem color*.—145B.

*Stem dimensions*.—10 to 20 mm in length with a diameter of 7 mm.

*Stem surface*.—Smooth.

*Internode length*.—5 mm.

Foliage:

*Type*.—Evergreen.

*Shape*.—Lanceolate.

*Cross-section*.—Concave.

*Division*.—Simple.

*Apex*.—Accuminate.

*Base*.—Obtuse.

*Venation*.—Pinnate.

*Vein color* (*adaxial surfaces*).—Darker than 143A.

*Vein color* (*abaxial surfaces*).—143A.

*Margins*.—Entire to undulate.

*Arrangement*.—Alternate.

*Attachment*.—Petiolate.

*Texture* (*adaxial & abaxial surface*).—Smooth and glossy.

*Hairiness* (*adaxial & abaxial surface*).—Glabrous.

*Mature leaf dimensions*.—Average length, 160 mm; width is 50 mm.

*Leaf color* (*adaxial surface*).—Darker than 141A.

*Leaf color* (*abaxial surface*).—146A.

*Petiole*.—Attitude — Erect to semi-erect. Strength — Moderately strong. Dimensions — Approximately 120 mm in length; width is approximately 7 to 9 mm. Color — Yellow-green, RHS 144B, and suffused with yellow-green, RHS 146D. Texture — Smooth and glabrous.

Inflorescence: To date, 'Phil01' has not flowered.

Bud: To date, 'Phil01' has not flowered.

Flower: To date, 'Phil01' has not flowered.

Reproductive organs: To date, 'Phil01' has not flowered.

Fruit and seed: To date, 'Phil01' has not flowered.

COMPARISONS WITH PARENT PLANTS

Plants of the new cultivar 'PHIL01' differ from the female parent in several ways. 'Phil01' has a short plant height whereas the parent grows approximately twice as tall and wide. Foliage of 'Phil01' has an entire to undulate margin whereas leaves of the female parent have a lobate margin. Furthermore, 'Phil01' exhibits a higher degree of basal branching when compared to the female parent.

COMPARISON WITH THE CLOSEST KNOWN VARIETY

Plants of the new cultivar 'PHIL01' are comparable to the commercial variety *Philodendron selloum* 'Winterbourne' (U.S. Pat. No. 7,030). However, 'Phil01' grows only to 30 cm tall whereas 'Winterbourne' may grow to 100 cm tall. Foliage of 'Phil01' is lanceolate with entire margins whereas 'Winterbourne' foliage is ovate with pinnatifid to lobate margins. Foliage of 'Phil01' is also smaller than that of 'Winterbourne'. Furthermore, 'Phil01' exhibits a higher degree of basal branching when compared to the 'Winterbourne'.

That which is claimed is:

1. A new and distinct variety of *Philodendron* plant named 'PHIL01', substantially as described and illustrated herein.

* * * * *

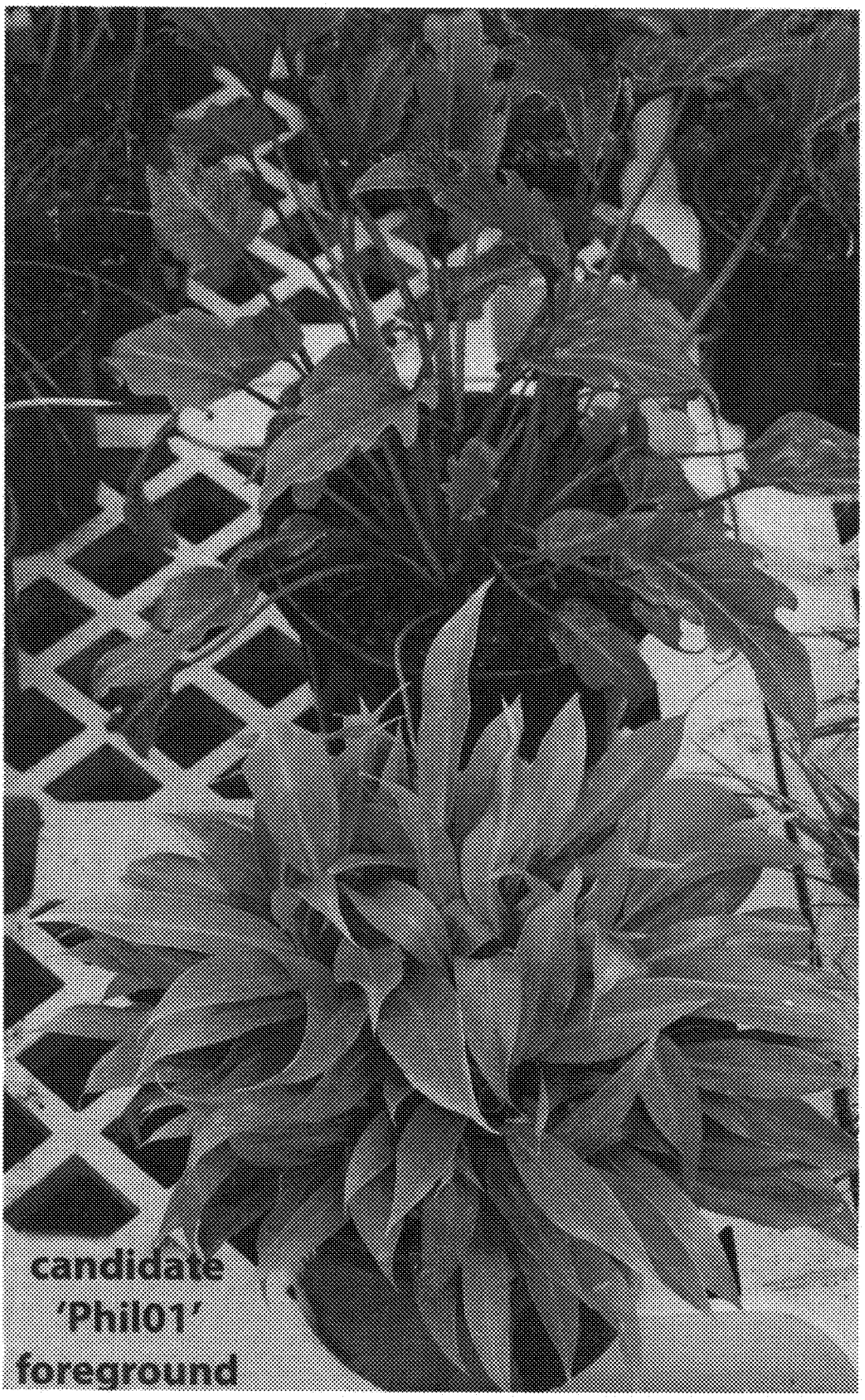
candidate
'Phil01'
foreground